United States Patent [19]  [11] 4,295,986
Gordon  [45] Oct. 20, 1981

[54] LOW TEMPERATURE CATALYTIC REDUCTION

[76] Inventor: Roy G. Gordon, 22 Highland St., Cambridge, Mass. 02138

[21] Appl. No.: 38,898

[22] Filed: May 14, 1979

[51] Int. Cl.$^3$ ............................ C07B 1/00; C09K 3/00
[52] U.S. Cl. .................................... 252/188; 423/283
[58] Field of Search ................ 252/188; 423/283, 342, 423/344

[56] References Cited

U.S. PATENT DOCUMENTS

| | | | |
|---|---|---|---|
| 3,043,857 | 7/1962 | Jenkner | 260/429.7 |
| 3,099,672 | 7/1963 | Cooper et al. | 260/448.2 |
| 3,460,906 | 8/1969 | Lonz | 252/188 |
| 3,496,206 | 2/1970 | Berger | 260/448.2 |
| 3,535,092 | 10/1970 | Chalk | 423/342 |
| 3,538,012 | 11/1970 | Goehrig | 252/188 |
| 3,634,277 | 1/1972 | Brown | 252/188 |

Primary Examiner—Leland A. Sebastian
Assistant Examiner—Irwin Gluck
Attorney, Agent, or Firm—Robert A. Cesari; John F. McKenna; Andrew F. Kehoe

[57] ABSTRACT

This invention relates to a method of utilizing alkali metal hydrides, such as sodium hydride and lithium hydride, under mild and safe conditions. The method may be used to produce bonds between hydrogen and elements such as carbon, silicon, germanium, tin, phosphorous, arsenic, antimony and tellurium. Many organic compounds, such as chlorides, bromides, ketones, aldehydes and acid chlorides, may also be reduced. The elements from the above list are bonded, before the reduction, to electronegative elements such as fluorine, chlorine, bromine, iodine, oxygen, sulfur, selenium and nitrogen.

According to the invention, the alkali metal hydride is catalytically activated by a solution of an alkali borohydride in a suitable ether solvent, so that it rapidly replaces the halogens or other electronegative groups by hydrogen atoms.

15 Claims, No Drawings

LOW TEMPERATURE CATALYTIC REDUCTION

BACKGROUND OF THE INVENTION

This invention relates to a novel, low temperature process for obtaining high yields of products using a catalytic hydride reduction method. Sodium hydride is a strong reducing agent, capable thermodynamically of entering into many hydride transfer reactions of the type:

$$NaH + MX \rightarrow MH + NaX, \qquad (1)$$

where M is a metal, metalloid or metalloid-containing radical, and X is an electronegative group; such as a halogen, alkoxy radical, etc.

However, in practice many such reactions take place too slowly to be useful. For example, it is well known in the art that sodium hydride fails to reduce chlorosilanes (for example, wherein $M = (CH_3)_3Si$, and $X = Cl$) at room temperature in the absence of catalysts. Since sodium hydride is the least expensive alkali metal hydride and is readily available commercially in large quantities, several investigations have been devoted to finding conditions under which its reduction potential could be utilized practically.

Using high temperatures (about 250 C), Cooper and Gilbert (U.S. Pat. No. 3,099,672) were able to successfully reduce chlorosilanes with sodium hydride at a practical rate, and with high conversion. However, this approach is restricted to cases in which both the reactants and products are stable at these high temperatures. Milder conditions were achieved by Chalk (U.S. Pat. No. 3,535,092), who discovered special catalytic solvents, such as hexamethylphosphoramide, in which chlorosilane reduction could be carried out at room temperature. However, this solvent is expensive, and also is a suspected carcinogen. Jenkner (U.S. Pat. No. 3,043,857) disclosed alkyl compounds of boron, aluminum and gallium which also catalyze reductions with sodium hydride. These catalysts have the disadvantage that they react violently with water, and are spontaneously flammable in air. Since both sodium hydride and the reduction products are flammable, the use of spontaneously flammable catalysts poses a severe fire hazard. Jenkner also mentions the non-pyrophoric alkoxy-and phenoxy-compounds of boron and aluminum as catalysts, but they are much less active than the pyrophoric alkyls, and require high temperatures (e.g., 150 C) and high concentrations to be effective. U.S. Pat. No. 3,496,206 discloses a somewhat similar process providing however, a less volatile catalyst form.

SUMMARY OF THE INVENTION

I have discovered that solutions of sodium borohydride in polyether solvents catalytically activate sodium hydride, so that it reacts quickly and completely with many compounds, even at room temperature. The stoichiometry follows equation (1) above, while the rate of reaction increases with the amount of sodium borohydride. The preferred solvents are polyethers such as diglyme (dimethyl ether of diethylene glycol, $CH_3OCH_2CH_2OCH_2CH_2OCH_3$), triglyme (dimethyl ether of triethylenene glycol, $CH_3OCH_2CH_2OCH_2CH_2OCH_2CH_2OCH_3$ or tetraglyme (dimethyl ether of tetraethylene glycol, $CH_3OCH_2CH_2OCH_2CH_2OCH_2CH_2OCH_2CH_2OCH_3$).

The process of the invention is run advantageously at ambient temperatures, e.g. 25–50 C. It is desirable that the process be carried out below 100 C at more elevated temperatures, there is an increasing danger of decomposition of the catalyst or the desired product.

It is thought that the observed reaction is catalyzed by a two-step cycle of reactions. First, the sodium borohydride catalyst transfers a single hydrogen atom to form the reduced product MH $$NaBH_4 + MX \rightarrow MH + NaX + BH_3 \cdot solvent \qquad (2)$$

The borane-solvent complex thus produced, then dissolves sodium hydride to regenerate the sodium borohydride catalyst, $$BH_3 \cdot solvent + NaH \rightarrow NaBH_4 + solvent \qquad (3)$$

which in turn produces more product by reaction (2). This catalytic cycle continues until all the NaH or MX is consumed.

Another reaction cycle which can aid the overall reaction is the following:

$$2NaBH_4 + MX \rightarrow MH + NaX + NaB_2H_7 \qquad (4)$$

$$NaB_2H_7 + NaH \rightarrow 2NaBH_4 \qquad (5)$$

Since both $NaB_2H_7$ and $BH_3 \cdot solvent$ are soluble in the polyether solvents, it is not easy to distinguish between these two possible cyclical mechanisms without detailed measurements of reaction kinetics. Indeed, both mechanisms may be simultaneously operative. In any case, applicant does not wish to be bound by the possible theories explaining the observed reduction reactions, but merely offers them as a possible aid in understanding the reactions.

In the presence of the preferred polyether solvents, the reduction is rapid, exothermic and complete at room temperature. In contrast, if monoethers, such as diethyl ether or tetrahydrofuran, are used as solvents, hardly any reaction takes place at all. This observation correlates with the known fact that sodium borohydride is almost completely insoluble in diethyl ether and tetrahydrofuran. The polyether monoglyme (dimethyl ether of ethylene glycol) is an intermediate case: some reductions are successful, but reaction is slower than in the higher polyethers, and the solubility of sodium borohydride is considerably lower (about 0.2 molar).

Not all polyethers are effective as catalytic solvents, however. For example, the diethyl ether of tetraethylene glycol, $CH_3CH_2OCH_2CH_2OCH_2CH_2OCH_2CH_2OCH_2CH_2OCH_2CH_3$, did not show much catalytic activity, and dissolved only about 0.06 molar sodium borohydride. Thus one may estimate that a reasonable catalytic solvent should dissolve at least 0.1 molar sodium borohydride, while a preferred solvent should form saturated solutions in excess of 1 molar sodium borohydride.

The polyether solvents should also be relatively pure and free of water, alcohols and other reducible substances. Commercially available solvents may be tested for purity by adding sodium borohydride and sodium hydride to a sample. If the solvent is pure, no bubbles or precipates form. If reaction does occur with impure solvent, more sodium borohydride and sodium hydride may be added until there is no more reaction. The mixture is filtered, and pure solvent is recovered by distillation. A stable stock solution (for example, 1 molar sodium borohydride in pure dry diglyme) may be prepared and stored indefinitely, provided it is protected from moisture and oxygen in the atmosphere.

The amount of sodium borohydride catalyst used is typically from about 0.4 to 1 molar concentration in the ether solvent used. Useful concentrations ordinarily range from about 0.2 to 2 molar. The practical upper limit to useful concentrations is determined by the solubility of the sodium borohydride in the polyether solvent. The lower limit to useful concentrations is determined by the speed of reaction. Ordinarily, concentrations of 0.1 molar or below are too slow to be practical, but may be useful if a very slow reaction is desirable, for example, for reasons of greater safety or easier temperature control. Indeed, the ability to control reaction speed to any desired value is an advantage of this method.

Excess sodium hydride should be present even at the end of the reduction reaction. If all the sodium hydride is consumed, reduction will continue with the sodium borohydride in solution, causing borane to build up in concentration, finally liberating spontaneously flammable diborane gas, and/or causing undesirable rearrangements of some reduction products.

Other alkali metals, such as lithium or potassium, may be used to partially or totally replace the sodium in the sodium hydride, or the sodium borohydride or both, in the reduction process. The use of lithium hydride and lithium borohydride catalyst, for example, widens the choice of solvent, since the lithium-based reaction goes smoothly in tetrahydrofuran or in diethyl ether, whereas the sodium-based reaction does not go at a practical rate in these more readily available monoether solvents. The success of the lithium reaction in these solvents appears to be due to the high solubility of lithium borohydride in tetrahydrofuran and in diethyl ether. Commercially available potassium hydride does not appear to react as smoothly as does sodium hydride, and thus potassium hydride appears to offer no significant advantages which might effect its higher cost.

ILLUSTRATIVE EMBODIMENTS OF THE INVENTION

In this application there are described preferred embodiments of the invention and suggested various alternatives and modifications thereof, but it is to be understood that these are not intended to be exhaustive and that other changes and modifications can be made within the scope of the invention. These suggestions herein are selected and included for purposes of illustration in order that others skilled in the art will more fully understand the invention and the principles thereof and will be able to modify it and embody it in a variety of forms, each as may be best suited in the condition of a particular case.

EXAMPLE 1

The reduction of silicon tetrachloride, $SiCl_4$, to silane, $SiH_4$, is carried out in a mechanically stirred and cooled reactor equipped with a dropping funnel for the gradual addition of liquid $SiCl_4$. Connected to the reactor is a cold trap for collection of volatile products. The outlet from the cold trap leads to a pressure relief device, such as an oil bubbler, which also isolates the reactor volume from the atmosphere. Before addition of any reagents, the reactor is cleaned and dried, and thoroughly purged with an atmosphere of dry nitrogen. A 1 molar solution of sodium borohydride in diglyme is added to fill the reactor to about ¼ of its capacity. An approximately equal volume of a 50% dispersion of sodium hydride in mineral oil is added, bringing the reactor filling to about ½ of its nominal capacity. If the resulting slurry cannot be stirred easily, a greater proportion of diglyme sould be used. Liquid nitrogen is added to the dewar vessel surrounding the cold trap. Silicon tetrachloride liquid is added slowly from the dropping funnel, along with rapid stirring and cooling to remove the heat of reaction. The rate of addition is kept low enough so that the temperature in the reactor does not rise appreciably above room temperature. Silane gas, $SiH_4$, is evolved and collected in the liquid nitrogen cooled trap. $SiCl_4$ is added until the sodium hydride has all reacted. The reaction yield is close to 100%.

EXAMPLES 2-5

Example 1 is repeated with the following liquid compounds substituted for the liquid $SiCl_4$:

| Ex | Reactant | Reduced Product | Boiling Point (°C.) of Product |
|---|---|---|---|
| 2 | $GeCl_4$ | $GeH_4$ | −88.5 |
| 3 | $PCl_3$ | $PH_3$ | −87.7 |
| 4 | $AsCl_3$ | $AsH_3$ | −55 |
| 5 | $CH_3SiCl_3$ | $CH_3SiH_3$ | −57.5 |

EXAMPLES 6-12

The apparatus of Example 1 is modified by the replacement of the oil bubbler seal with a cold trap and a vacuum pump, so that products with higher boiling points may be distilled out of the reaction vessel even without heating, after reduction is complete. (During reduction the vacuum pump is not operated, in order not to lose any of the volatile borane catalyst.) The procedure of Example 1 is repeated with the following liquid compounds substituted for the liquid $SiCl_4$:

| Ex | Reactant | Product | Boiling Point (°C.) of Product |
|---|---|---|---|
| 6 | $(CH_3)_2SiCl_2$ | $(CH_3)_2SiH_2$ | −20 |
| 7 | $SbCl_5$ | $SbH_3$ | −17.1 |
| 8 | $SiCl_6$ | $Si_2H_6$ | −14.5 |
| 9 | $(CH_3)_3SiCl$ | $(CH_3)_3SiH$ | 7 |
| 10 | $(CH_3)_2SiClSiCl_2CH_3$ | $(CH_3)_2SiHSiH_2CH_3$ | 68.5 |
| 11 | $(CH_3)_3SiSiCl_2CH_3$ | $((CH_3)_3SiSiH_2CH_3$ | 80 |
| 12 | $((CH_3)_2SiCl)_2$ | $((CH_3)_2SiH)_2$ | 86 |

EXAMPLES 13-16

Example 6 is repeated with solutions of the following solid compounds in diglymer, substituted for the liquid $(CH_3)_2SiCl_2$:

| Ex | Reactant | Reduced Product | Boiling Point (°C.) |
|---|---|---|---|
| 13 | $SbCl_3$ | $SbH_3$ | −17.1 |
| 14 | $TeCl$ | $H_2Te$ | −2.2 |
| 15 | $(CH_3)_3SnCl$ | $(CH_3)_3SnH$ | 60 |
| 16 | $(CH_3)_2SnCl_2$ | $(CH_3)_2SnH_2$ | 35 |

EXAMPLE 17

The apparatus described in Examples 6–12 is modified by replacing the dropping funnel for addition of liquids, with a tube for gradual addition of powder or small crystalline solid materials. The reductions of Examples 13–16 are repeated, by adding the solid materials directly, rather than in solution. Because of the smaller amount of solvent used, the products are removed more quickly, and larger amounts may be reduced in one run.

EXAMPLE 18

If the hydride product does not react with or dissolve in water, then the product may be isolated by washing with water, rather than by distillation. $((CH_3)_2SiCl)_2$ is reduced as in the previous examples except that the reduced product $((CH_3)_2SiH)_2$ is not distilled out of the reactor. Also, dry powdered sodium hydride without a protective mineral oil is used, so that the mineral oil will not contaminate the product. After reaction is complete, the contents of the reactor are filtered to remove excess NaH and carefully hydrolyzed with ice. The product, i.e. tetramethyldisilane, separates as an upper layer floating on the lower aqueous layer. The aqueous layer contains the diglyme, salt and sodium borohydride.

EXAMPLE 19

The procedure of Example 18 is repeated except that (a) a 1 molar solution of lithium borohydride in tetrahydrofuran is used as the catalyst and (b) powdered lithium hydride is suspended in this solution.

A product such as that obtained in Example 18 is obtained by washing the product with water to remove the water-soluble tetrahydrofuran and salt.

EXAMPLE 20 to 26

The processes described in Examples 6 to 12 are repeated using tetraglyme (boiling point of 276° C.) as the solvent. Excellent yields of essentially similar product are obtained in each instance.

EXAMPLE 27

Example 1 is repeated using potassium borohydride and potassium hydride instead of the sodium products. The process yields substantially the same product as does Example 1.

To illustrate the importance of the low temperature aspect of the invention, is noted that the reactions described above in Examples 2, 7, 8, 10, 11, 12, 13, 14, 15 and 16 would involve undesirable decomposition or rearrangement of either reactant or desired product were they run at the elevated temperatures of the prior art, e.g. 150° C. to 300° C.

It is further to be understood that the following claims are intended to cover all of the generic and specific features of the invention herein described.

What is claimed as new and desired to be secured by Letters Patent of the United States is:

1. A process for reducing compounds having reducible electronegative functionality, said process comprising the step of carrying out said reduction in a reaction medium which comprises a reducing agent which is a hydride of an alkali metal, and a catalyst which is the borohydride of an alkali metal, and an ether solvent in which the borohydride catalyst is soluble.

2. A process as in claim 1, in which the ether is selected from the class of methyl ethers of poly (ethylene glycols).

3. A process as in claim 2, in which the ether is diglyme, triglyme or tetraglyme.

4. A process as in claim 1, in which the alkali metal is lithium, sodium, or potassium.

5. A process as in claim 1 wherein the alkali metal is lithium and the ether is diethyl ether or tetrahydrofuran.

6. A process as in claim 1, 2, 3, 4 or 5, in which the compound to be reduced contains at least one element selected from the class consisting of carbon, silicon, germanium, tin, phosphorus, arsenic, antimony, and tellurium, and that element is bonded to a more electronegative element selected from the class consisting of fluorine, chlorine, bromine, iodine, oxygen, sulfur, selenium, and nitrogen.

7. A process as in claim 1, 2, 3, 4 or 5 in which the compound to be reduced comprise a readily-reduced organic compound comprising a halide, ketone, aldehyde, acid chloride or other reducible electronegative functional group.

8. A process as in claim 1, 2, 3, 4 or 5 in which the compound to be reduced is a silicon halide.

9. A process as in claim 1, 2, 3, 4 or 5 in which the compound to be reduced is a tin halide.

10. A process as defined in claim 1, 2 or 4 wherein said ether is selected from ethers in which at least 0.1 molar quantity of sodium borohydride is soluble and wherein the compound to be reduced in a silicon halide or a tin halide, and wherein the reduction is carried out below 100° C.

11. A process as defined in claim 1, 2, 3, 4, or 5 wherein the reduction is carried out below 100° C.

12. A process as defined in claim 1, 2, 3, 4, or 5 wherein the reduction is carried out below 50° C.

13. A composition useful in effecting the catalytic reduction of organic halides and the like, said composition comprising,
   (1) an ether solvent for an alkali metal borohydride,
   (2) an effective quantity of an alkali metal hydride reducing agent, and
   (3) a catalytic quantity of the borohydride of an alkali metal.

14. A composition as defined in claim 1 wherein the ether is a methyl ether of poly (ethylene glycol) and is one capable of forming a saturated solution in excess of 1 molar sodium borohydride.

15. A process for reducing a chemical compound having electronegative functionality said process comprising the step of dissolving a borohydride of an alkali metal in an ether solution to form a reaction medium, activating, in said reaction medium, a sodium hydride reducing agent with said borohydride; carrying out said reduction of said chemical compound in said reaction medium, and wherein a complex compound is formed by said solvent and a borane reaction product of said borohydride such that borohydride is regenerated by a reaction a said complex compound and said hydride.

* * * * *

UNITED STATES PATENT AND TRADEMARK OFFICE
CERTIFICATE OF CORRECTION

PATENT NO. : 4,295,986
DATED : October 20, 1981
INVENTOR(S) : Roy G. Gordon

It is certified that error appears in the above-identified patent and that said Letters Patent are hereby corrected as shown below:

Column 4, line 49 - Change "$SiCl_6$" to --$Si_2Cl_6$--;

Column 4, line 58 - Change "solid compounds in diglymer" to --solid compounds in diglyme--.

Signed and Sealed this

Twenty-second Day of December 1981

|SEAL|

Attest:

GERALD J. MOSSINGHOFF

Attesting Officer    Commissioner of Patents and Trademarks